United States Patent [19]

Ashmore et al.

[11] Patent Number: 4,894,479
[45] Date of Patent: Jan. 16, 1990

[54] HERBICIDAL DIPHENYL ETHERS

[75] Inventors: John W. Ashmore, North Wales; Ted Fujimoto, Churchville, both of Pa.

[73] Assignee: Rohm and Haas Company, Philadelphia, Pa.

[21] Appl. No.: 269,224

[22] Filed: Jun. 1, 1981

[51] Int. Cl.$^4$ ............................................. C07L 53/00
[52] U.S. Cl. ...................................... 564/300; 560/21; 560/29; 71/105; 71/121; 71/116; 558/416; 558/413
[58] Field of Search .......................... 71/121, 116, 105; 260/453 R; 560/21; 564/300

[56] References Cited

U.S. PATENT DOCUMENTS 3,282,991 11/1966 Klein et al. ............................ 560/21
4,200,587 4/1980 Suchy ..................................... 560/61

FOREIGN PATENT DOCUMENTS 0013660 7/1980 European Pat. Off. .............. 560/21

Primary Examiner—Paul J. Killos
Attorney, Agent, or Firm—T. P. Strobaugh

[57] ABSTRACT

This invention is directed to diphenyl ethers having in the 3' position a radical of the formula:

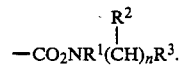

The products are prepared by reacting a 3'-halocarbonyl compound with an appropriate substituted hydroxyl amine. These compounds and their agronomically acceptable salts and compositions containing these compounds as active ingredients are selective herbicides.

11 Claims, No Drawings

HERBICIDAL DIPHENYL ETHERS

This invention relates to nitrodiphenyl ethers, compositions containing nitrodiphenyl ethers and methods of controlling weeds.

Diphenyl ethers are known to be effective weed control agents. See, for example, U.S. Pat. Nos. 3,928,416; 3,454,392; 3,798,276; 3,873,303; 4,001,005; and 4,029,493 among the many patents issued. See also U.S. Pat. No. 4,200,587 and E. P. No. 13-660. However, even now herbicidal effectiveness of a diphenyl ether cannot be predicted knowing only the structure and often quite closely related compounds will have quite different weed control abilities. See, *Advances in Agronomy*, Vol. 24, pages 331, 332, 355, 356, 357 and 358, *Herbicides, Chemical Degradation and Mode of Action*, Kearney and Kaufman, Vol. 2, Dekker, Inc. pages 552–563 and 728–737 and *Mode of Action of Herbicides*, Ashton and Crafts and, also, U.S. Pat. Nos. 3,454,392 and 3,776,961.

An ideal herbicide should give selective weed control over the full growing season, with a single administration at low rates of application. It should be able to control all common weeds by killing them as the seed, the germinating seed, the seedling, and the growing plant. At the same time, the herbicide should be substantially nonphytotoxic to the crops to which it is applied and should decompose or otherwise be dissipated so as not to poison the soil permanently. The known diphenyl ether herbicides fall short of these ideals and thus the search continues to discover new herbicides which are more selective or which complement the known diphenyl ethers.

In accordance with the present invention, there is provided a class of diphenyl ethers having the formula:

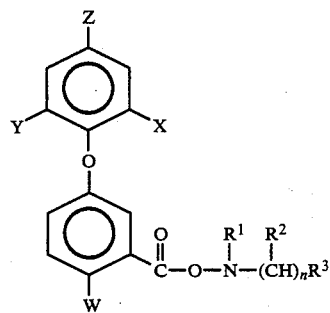

wherein X is hydrogen, halo, such as chloro, fluoro, bromo, iodo and the like, trihalomethyl, such as trifluoromethyl and the like; alkyl, for example, lower alkyl of from 1 to 6 carbon atoms, nitro or cyano; is hydrogen or halo such as chloro, bromo, fluoro, iodo, and the like; Z is halo, such as chloro, bromo, fluoro and the like, trihalomethyl, such as trifluoromethyl, pentahaloethyl, such as 1,1,1-trifluoro-2,2-difluoroethyl and the like; W is nitro, cyano, halo, such as chloro, bromo, fluoro, iodo and the like or a radical of the formula: $S(O)_{n'}R$, wherein R is lower alkyl of from 1 to 6 carbon atoms, such as methyl, ethyl, propyl, butyl, pentyl and the like or trihaloalkyl, such as trifluoromethyl and the like; n' has a value of from 0-2; $R^1$ is hydrogen or a substituted or unsubstituted, saturated or unsaturated hydrocarbyl radical for example, alkyl, such as lower alkyl of from 1 to 6 carbon atoms, alkenyl, such 5 as lower alkenyl of from 3 to 5 carbon atoms, alkynyl, such as lower alkynyl of from 3 to 5 carbon atoms and the like; $R^2$ is hydrogen or lower alkyl; n has a value of 0 to 3; $R^3$ is substituted or unsubstituted radical including alkoxycarbonyl, for example, lower alkoxycarbonyl, wherein the alkoxy moiety has from 1 to 6 carbon atoms; alkylcarbonyl, for example, lower alkylcarbonyl, wherein the alkyl moiety has from 1 to 6 carbon atoms; aminocarbonyl; mononuclear aryloxy, for example, phenoxy and the like or carboxy including the agronomically acceptable amides, esters and salts thereof; or $R^1$ and $R^2$ may be joined together with the nitrogen to which they are attached to form a heterocyclic ring containing one nitrogen atom and from 4 to 8 nuclear carbon atoms, such as pyrrolidyl, piperidyl, hexamethyleneiminyl, heptamethyleneiminyl, octamethyleneiminyl and the like.

The term "alkyl" or "alkoxy" includes both the straight and branch chained hydrocarbon groups containing from 1 to 6 carbon atoms, such as methyl, ethyl, propyl, isopropyl, butyl, isobutyl, tert-butyl, methoxy, ethoxy, propoxy, isopropoxy, butoxy, isobutoxy, tert-butoxy and the like.

The terms "alkenyl" and "alkynyl" include both straight and branched chain unsaturated hydrocarbon groups such as, allyl, butenyl, isobutenyl, pentenyl, isopentyl and the like and propargyl, butynyl, isobutynyl, pentynyl and the like. When the $R^1$ and/or $R^3$ radicals are substituted, the substituents can be those selected from halo, cyano, hydroxy, alkoxy, alkylthio, alkylsulfinyl, alkylsulfonyl, alkylcarbonyl, alkoxycarbonyl, aminocarbonyl, trifluoromethyl, nitro, alkylamino, carboxy and agronomically acceptable salts, esters and amides thereof.

Preferred compounds of this invention are those wherein $R^1$ is hydrogen, lower alkyl, lower alkenyl or lower alkynyl; $R^2$ is hydrogen; $R^3$ is lower alkoxycarbonyl or lower alkylcarbonyl and n has a value of 0 to 1.

Preferred compounds are:
(2-methoxycarbonyl-N-hydroxypyrrolidinyl)-5-(2-methyl-4-trifluoromethylphenoxy)-2-trifluoromethanesulfonylbenzoate;
N-(methoxycarbonylmethyl)aminooxy-5-(2-chloro-4-trifluoromethylphenoxy)-2-nitrobenzoate;
N-methyl-N-(2-ethoxycarbonylethyl)aminooxy-5-(2-nitro-4-pentafluoroethylphenoxy)-2-cyanobenzoate;
N-(carboxymethyl)aminooxy-5-(2-cyano-4-chlorophenoxy)-2-bromobenzoate sodium salt;
N-methoxycarbonylmethyl-N-(2-methoxyethyl)aminooxy-5-(4-trifluoromethylphenoky)-2-nitrobenzoate;
N-(2-chloroethyl)-N-(2-ethoxycarbonylethyl)aminooxy-5-(2,6dichloro-4-pentafluoroethylphenoxy)-2-cyanobenzoate;
N-methoxycarbonyl-N-12-methoxyethyl)aminooxy-5-(2,4-dichlorophenoxy)-2-idobenzoate;
N-ethoxycarbonyl-N-(2-ethylthioethyl)aminooxy-5-(2-trifluoromethyl-4-bromophenoxy)-2-methanesulfonylbenzoate;
N-ethoxycarbonyl-N-(cyanomethyl)aminooxy-5-(2-methyl-4-trifluoromethylphenoxy)-2-trifluoromethanesulfonylbenzoate;
N-methyl-N-(2-methanesulfonylethyl)aminooxy-5-(2-nitro-4-pentafluoroethylphenoxy)-2-cyanobenzoate;
N-acetylaminooxy-5-(2-chloro-4-trifluoromethylphenoxy)-2-nitrobenzoate;

N-formylaminooxy-5-(2-cyano-4-chlorophenoxy)-2-chlorobenzoate;
N-dimethylaminocarbonyl-N-methylaminooxy-5-(4-trifluoromethylphenoxy)-2-nitrobenzoate;
N-methanesulfonylaminooxy-5-(2-chloro-4-trifluoromethylphenoxy)-2-nitrobenzoate;
N-methanesulfinylaminooxy-5-(2,6-dichloro-4-trifluoromethylphenoxy)-2-cyanobenzoate;
N-(4-chlorophenyl)aminooxy-5-(2,4-dichlorophenoxy)-2-nitrobenzoate;
N-methoxycarbonylaminooxy-5-(2-chloro-4-trifluoromethylphenoxy)-2-nitrobenzoate;
N-ethoxycarbonyl-N-methylaminooxy-5-(2-chloro-4-trifluoromethylphenoxy)-2-nitrobenzoate;
N-ethoxycarbonyl-N-allylaminooxy-5-(2-chloro-4-trifluoromethylphenoxy)-2-nitrobenzoate;
N-methoxycarbonyl-N-(3-ethoxycarbonyl-2-propenyl)aminooxy-5-(4-trifluoromethylphenoxy)-2-nitrobenzoate;
N-propoxycarbonyl-N-(2-propynyl)aminooxy-5-(2,6-dichloro-4-pentafluoroethylphenoxy)-2-cyanobenzoate;
N-(2-propoxycarbonyl)-N-(2-chloroethyl)aminooxy-5-(2,4-dichlorophenoxy)-2-iodobenzoate;
N-(tert-butoxycarbonyl)-N-(methoxycarbonylmethyl)aminooxy-5-(2-trifluoromethyl-4-chlorophenoxy)-2-methanesulfonylbenzoate;
N-(ethoxycarbonylmethylcarbonyl)aminooxy-5-(2-fluoro-4-chlorophenoxy)-2-methanesulfonylbenzoate;
N-(1-propoxycarbonylethyl)-N-(2-propenyl)-aminooxy-5-(2-methyl-4-chlorophenoxy)-2-nitrobenzoate;
N-(3-t-butoxycarbonylpropyl)-N-(2-propynyl)aminooxy-5-(2-nitro-4-chlorophenoxy)-2-iodobenzoate;
N-methoxycarbonyl-N-methylaminooxy-5-(2-cyano-4-trifluoromethylphenoxy)-2-nitrobenzoate;
N-methoxycarbonyl-N-methylaminooxy-5-(2,6-dichloro-4-trifluoromethylphenoxy)-2-cyanobenzoate; and
N-acetyl-N-methylaminooxy-5-(2,4,6-trichlorophenoxy)-2-nitrobenzoate.

In general, the diphenyl ethers of this invention, I, supra) may be prepared by reacting an appropriately substituted diphenyl ether (II, infra) with an appropriate hydroxyl amine (III, infra) as illustrated by the following reaction:

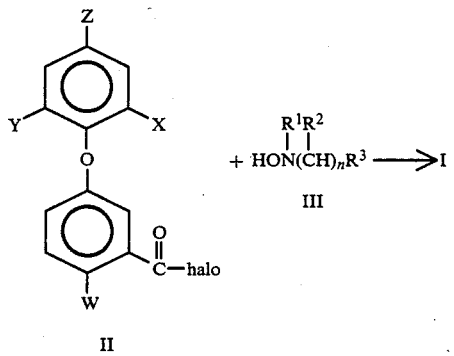

wherein W, X, Y, Z, $R^1$, $R^2$, $R^3$ and n are as defined above and halo is preferably chloro.

This reaction is conducted at a temperature in the range of from about 0° to 50° C. in a suitably inert solvent for example, ether type or halogenated hydrocarbons such as, tetrahydrofuran, diethyl ether, dichloromethane, chloroform, carbon tetrachooride, also, ketones such as acetone, methylethyl ketone and the like. A base is employed as an "acid scavanger" such as aromatic or tertiary amines including pyridine, lutidene, collidene, triethyl- or trimethyl amine and the like.

The hydroxyl amines (III, supra) are either known compounds or can be prepared by the following procedure in Houben-Weyl *Methoden der Organishen Chemie* 10/1 p. 1097.

The diphenyl ethers (I, supra) of the invention are useful as preemergence and postemergence herbicides. Preemergence herbicides are ordinarily used to treat the soil by application either before seeding, during seeding, or after seeding and before the crop emerges. Postemergence herbicides are those which are applied after the plants have emerged. The compounds of this invention are especially active as pre-emergence herbicides.

Among the crops on which the diphenyl ethers of the invention can be advantageously employed are: cotton, soybeans, peanuts, beans, peas, carrots, corn, wheat, rice, and other cereal crops.

The diphenyl ethers (I, supra) can be applied in any amount which will give the required control of weeds. A standard rate of application of the herbicides of the invention is in the range of from about 0.02 to about 12 pounds of diphenyl ether per acre. A preferred range is from about 0.1 to about 4 pounds per acre.

Under some conditions, the diphenyl ethers (I, supra) may be advantageously incorporated into the soil or other growth medium prior to planting a crop. This incorporation can be by any convenient means, including simple mixing with the soil, applying the diphenyl ether to the surface of the soil and then disking or dragging into the soil to the desired depth, or by employing a liquid carrier.

The diphenyl ethers of the invention can be applied to the growth medium or to plants to be treated either neat or as a component in a herbicidal composition or formulation which also comprises an agronomically acceptable carrier. "Agronomically acceptable carrier" is any carrier which can be used to dissolve, disperse or diffuse a herbicidal compound in the composition without impairing the effectiveness of the herbicidal compound and which by itself has no permanent deterimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers 1969 Annual."

Examples of solvents which are useful in the practice of this invention include alcohols, ketones, aromatic hydrocarbons, dimethyl formamide, dioxane, dimethyl sulfoxide, and the like. Mixtures of these solvents can also be employed. The concentration of the solution can vary from about 2% to about 98% of active product with a preferred range being from about 25% to about 75%.

For the preparation of emulsifiable concentrates, the diphenyl ether can be dissolved in organic solvents, such as toluene, xylene, methylated naphthalene, corn oil, pine oil, isophorone, cyclohexanone, methyl oleate, and the like, or in mixtures of these solvents, together with an emulsifying agent which permits dispersion in water. Suitable emulsifiers include, ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts or alkylbenzenesulfonates and the fatty alcohol sodium sulfates, having surface-active properties can be used as emulsifiers reaction product. Flowable concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually from about 10% to 60% and in flowable emulsion concentrates, can be as high as about 75%.

Wettable powders suitable for spraying, can be prepared by admixing the compound with a finely divided solid, such as clays, inorganic silicates and carbonates, and silicas and then incorporating wetting agents, sticking agents, and/or dispersing agents. The concentration of active ingredients in such formulations is usually in the range of from about 20% to about 98%, and, preferably, from about 40% to about 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted from about 1% to about 10% use concentration.

Granular formulations can be prepared by impregnating a solid, such as granular fuller's earth, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size in the range of from about 16 to 60 mesh. The diphenyl ether will usually comprises from about 2 to about 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low-gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Salts and Ester Derivatives Thereof 2,3,6-trichlorobenzoic acid, 2,3,5,6-tetrachlorobenzoic acid, 2-methoxy-3,5,6-trichlorobenzoic acid, 2-methoxy-3,6-dichlorobenzoic acid, 2-methyl-3,6-dichlorobenzoic acid, 2,3-dichloro-6-methylbenzoic acid, 2,4-dichlorophenoxyacetic acid, 2,4,5-trichlorophenoxyacetic acid, 2-methyl-4-chlorophenoxyacetic acid, 2-(2,4,5-trichlorophenoxy) propionic acid, 4-(2,4-dichlorophenoxy) butyric acid, 4-(2-methyl-4-chlorophenoxy) butyric acid, 2,3,6-trichlorophenylacetic acid, 3,6-endoxohexahydrophthalic acid, dimethyl 2,3,5,6-tetrachloroterephthalate, trichloroacetic acid, 2,2-dichloropropionic acid, 3-amino-2,5-dichlorobenzoic acid, 2,3-dichloroisobutyric acid.

Carbamic Acid Derivatives ethyl N,N-Di(n-propylthiocarbamate, propyl N,N-di-(n-propyl) thiocarbamate, ethyl N-ethyl-N-(n-butyl) thiocarbamate, ethyl N-ethyl-N-(n-butyl)thiocarbamate, propyl N-ethyl-N-(-butyl)thiocarbamate, 2-chloroallyl N,N-diethyldithiocarbamate, N-methyldithiocarbamic acid salts, ethyl 1-hexamethyleneiminecarbothiolate, isopropyl N-phenylcarbamate, isopropyl N-(m-chlorophenyl carbamate, 4-chloro-2-butynyl N-(m-chlorophenyl carbamate, methyl N-(3,4-dichlorophenyl) carbamate, methyl-m-hydroxycarbanilate-m-methylcarbanilate, S-(4-chlorobenzyl)-N,N-diethylthiocarbamate.

Phenols dinitro-o-(sec-butyl) phenol and its salts, pentachlorophenol and its salts

Substituted Ureas 3-(3,4-dichlorophenyl)-1,1-dimethylurea, 3-phenyl-1,1-dimethylurea, 3-(3,4-dichlorophenyl)-3-methoxy-1,1-dimethylurea, 3-(4-chlorophenyl)-3-methoxy-1,1-dimethylurea, 3-(3,4-dichlorophenyl)-1-n-butyl-1-methylurea, 3-(3,4-dichlorophenyl)-1-methoxy-1-methylurea, 3-(4-chlorophenyl)-1-methoxy-1-methylurea, 3-(3,4-dichlorophenyl)-1,1,3-trimethylurea, 3-(3,4-dichlorophenyl)-1,1-diethylurea, dichloral urea, N'[4-[2-p-methylphenyl)ethoxy]phenyl]-N-methoxy-N-methylurea,1,1,3-trimethyl-3-(5-p-chlorobenzylthio-1,3,4-thiadyazol-2-yl)urea, 3-[-chlorophenoxy)phenyl]-1,1-dimethylurea.

Substituted Triazines 2-chloro-4,6-bis(ethylamino)-s-triazine, 2-chloro-4-ethylamino-6-isopropylamino-m-triazine, 2-chloro-4,6-bis(methoxypropylamino)-s-triazine, 2-methoxy-4,6-bis-(isopropylamino)-s-triazine, 2-chloro-4-ethylamino-6-(3-methoxypropylamino)-s-triazine, 2-methylmercapto-4,6-bis-(ethylamino)-s-triazine, 2-methylmercapto-4-ethylamino-6-isopropylamino-s-triazine, 2-chloro-4,6-bis(isopropylamino)-s-triazine, 2-methoxy-4,6-bis(ethylamino)-s-triazine, 2-methoxy-4-ethylamino-6-isopropylamino-s-triazine, 2-methylmercapto-4-(2-methoxyethylamino)-6-isopropylamino-s-triazine.

Diphenyl Ether Derivatives 2,4-dichloro-4'-nitrodiphenyl ether, 2,4,6-trichloro-4'-nitrodiphenyl ether, 2,4-dichloro-6-fluoro-4'-nitrodiphenyl ether, 2-chloro-4-trifluoromethyl-3'-carboxy-4'-nitrodiphenyl-ether and its salt and ester derivatives, 3-methyl-4'-nitrodiphenyl ether, 3,5-dimethyl-4'-nitrodiphenyl ether, 2,4'-dinitro-4-trifluoromethyldiphenyl ether, 2,4-dichloro-3'-methoxy-4'-nitrodiphenyl ether, sodium 5-(2-chloro-4-trifluoromethylphenoxy)-2-nitrobenzoate.

Anilides

N-(3,4-dichlorophenyl)propionamide, N-(3,4-dichlorophenyl) methacrylamide, N-(3-chloro-4-methylphenyl)-2-methylpentamide, N-(3,4-dichlorophenyl)trimethylacetamide, N-(3,4-dichlorophenyl) $\beta,\beta$-dimethylvaleramide, N-isopropyl-N-phenylchloroacetamide, N-n-butoxymethyl-N-(2,6-diethylphenyl)chloroacetamide and N-n-methoxymethyl-N-(2,6-diethylphenyl)chloroacetamide, 2-chloro-N-(2-ethyl-6-methylphenyl)-N-(2-methoxy-1-methylethyl) acetamide.

Uracils 5-bromo-3-s-butyl-6-methyluracil, 5-bromo-3-cyclohexyl-1,6-dimethyluracil, 3-cyclohexyl-5,6-trimethyleneuracil, 5-bromo-3-isopropyl-6-methyluracil and 3-tertbutyl-5-chloro-6-methyluracil.

Nitriles 2,6-dichlorobenzonitrile, diphenylacetonitrile, 3,5-dibromo-4-hydroxybenzonitrile, and 3,5-diiodo-4-hydroxybenzonitrile.
Other Organic Herbicides

Other Organic Herbicides 2-chloro-N,N-diallylacetamide, N-(1,1-dimethyl-2-propynyl)-3,5-dichlorobenzamide, maleic hydrazide, 3-amino-1,2,4-triazole, monosodium methanearsonate, N,N-diallyl-2-chloroacetamide, disodium methanearsonate, N,N-dimethyl-$\beta,\beta,$-diphenylacetamide, N,N-di(-propyl)-2,6-dinitro-4-trifluoromethylaniline, N,N-di(n-propyl)-2,6-dinitro-4-methylaniline, N,N-di(n-propyl)-2,6-dinitro-4-methylsulfonylaniline, $N^3,N^3$-di-n-propyl-2,4-dinitro-6-trifluoromethyl-m-phenylenediamine, 3,5-dinitro-$N^4N^4$-dipropylsulfanilamide, 4-isopropyl-2,6-dinitro-N,N-dipropylaniline, N-(2-chloroethyl)-2,6-dinitro-N-propyl-4-trifluoromethylaniline, O-(2,4-dichlorophenyl)-0-methylisopropylphosphoramidothioate, 4-amino-3,5,6-trichloropicolinic acid, 2,3-dichloro-1,4-naphthoquinone, di-(methoxythiocarbonyl)disulfide, 3-isopropyl-1H-2,1,3-benzothiadiazine(4)3H-one-2,2,dioxide, 6,7-dihydrodipyridol-[1,2-a:a',1'-c]pyrazidinium salts, 1,1'-dimethyl-4,4'-bipyridinium salts and 3,4,5,6-tetrahydro-3,5-dimethyl-2-thio-2H-1,3,5-thiadizine, 2-naphthoxy)-N-diethylacetamide, 2-N-(1-naphthylaminocarbonyl)benzoic acid, 3-isopropyl-1H-2,1,3-benzothiadiazine-4(3H)-one 2,2-dioxide, methyl-2-[4-(4chlorophenoxy)phenoxy]propionate, methyl-2-[4-(3,5-dichloropyrid-2-yl)phenoxy]-propionate, 2-[1-(allyloxyamino)propylidene]4-carbomethoxy-5,5-dimethylcyclohexane-1,3-dione.

When mixtures of herbicides are employed, the relative proportions which are used will depend upon the drop to be treated and the degree of selectivity in weed control desired.

The following examples will further illustrate this invention but are not intended to limit it in any way.

EXAMPLE 1

N-Ethoxycarbonylaminooxy-5-(2-chloro-4-trifluoromethylphenoxy)-2-nitrobenzoate

To an ice-cooled solution of 5-(2-chloro-4-trifluoromethylphenoxy)-2-nitrobenzoyl chloride (7.6 g., 20 mmol.) in 70 ml. dichloromethane was added pyridine (2.5 g., 30 mmol.). A mild exothermic reaction ensued and a voluminous precipitate formed. The slurry was stirred an additional 30 minutes with ice bath cooling then N-hydroxyurethane (2.3 g., 22 mmol.) was added. The reaction mixture became homogeneous, the ice bath was removed and the reaction mixture stirred overnight. The reaction mixture was worked-up by washing first with 3M HCL (2×30 ml.) then saturated NaHCO$_3$ (30 ml.) and drying the organic phase with anhydrous MgSO$_4$. Concentration under reduced pressure affords 9.0 g. of an off-white solid. Crystallization of the crude product with ethyl acetate/hexane affords 4.7 g. of an off-white solid, mp 125°–128° C.

EXAMPLE 2

N-Ethoxycarbonyl-N-methylaminooxy-5-(2-chloro-4-trifluoromethylphenoxy)-2-nitrobenzoate By following substantially the procedure of Example 1 and by employing the following amounts:
7.6 g, (20 mmol.) of 5-(2-chloro-4-trifluoromethylphenoxy)-2-nitrobenzoylchloride;
2.5 g, (30 mmol.) of pyridine;
2.5 g, (21 mmol.) of N-hydroxy-N-methylurethane; and
20 ml. of dichloromethane
there is obtained 6.3 g of product as off-white solid mp 80°–83° C.

Test Procedure

This example shows the herbicidal activity of the diphenyl ethers of the invention exhibited on the following representative species:

|  |  |  | Approx. No. Seeds |
|---|---|---|---|
| Monocots: | Barnyardgrass | (Echinochloa crusgalli) | 25 |
|  | Downybrome | (Bromus tectorum) | 20 |
|  | Foxtail | (Setaria spp) | 25 |
|  | Johnsongrass | (Sorghum Halepense) | 25 |
|  | Nutsedge | (Cyperus esculentus) | 5 |
|  | Wild Oat | (Avena fatua) | 20 |
| Dicots | Cocklebur | (Xanthium pensyl- | 3 |

| | | Approx. No. Seeds |
|---|---|---|
| | vanicum) | |
| Marigold | (Tagetes spp) | 15 |
| Morning Glory | (Ipomoea spp) | 10 |
| Tomato | (Lycoperiscon esculentum) | 15 |
| Velvetleaf | (Abutilon theophrasti) | 15 |
| Sickle pod | (Cassia obtusifolia) | 6 |

The following test procedure is employed. Seeds of the above species are planted in soil in trays (approx. 7"×10½"×3"). For preemergence tests, the trays are sprayed with the test compound immediately after planting. For postemergence tests, the seeds are allowed to germinate and after growing in the greenhouse for two weeks, the growing plants are treated with the test compound. The compound to be evaluated is dissolved in acetone or water and sprayed over the trays using a carrier volume equivalent to 50 gallons per acre at the rate of application (in pounds per acre, lb/A) specified in the table. About two weeks after application of the test compound, the state of growth of the plants is observed and the phytotoxic effect of each compound determined as follows: each species is evaluated on a scale of 0-100 in which 0=no activity and 100=total kill and the results for the monocots (M) and dicots (D) separately averaged. The following table shows the results obtained for the compounds of the invention at 2 lb/A., ½ lb/A. and ¼ lb./A.

| HERBICIDAL DATA | | | | | | |
|---|---|---|---|---|---|---|
| | PRE | | | | | |
| | ¼ | | ½ | | 2 | |
| | M | D | M | D | M | D |
| Ex. 1 | 48 | 65 | 74 | 83 | 83 | 98 |
| Ex. 2 | 6 | 20 | 26 | 51 | 48 | 62 |
| | POST | | | | | |
| | ¼ | | ½ | | 2 | |
| | M | D | M | D | M | D |
| Ex. 1 | 13 | 34 | 20 | 64 | 48 | 79 |
| Ex. 2 | 2 | 23 | 13 | 50 | 24 | 71 |

One skilled in the art will appreciate that the above examples are merely illustrative and are capable of a wide variation and modification without departing from the spirit of this invention as defined by the following claims.

What is claimed is:

1. A compound of the formula

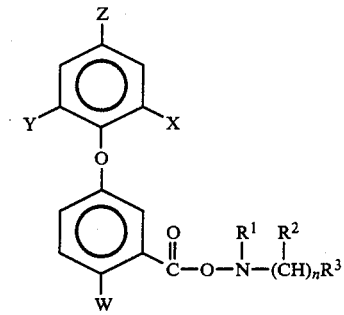

wherein X is hydrogen, halo, trihalomethyl, alkyl, nitro or cyano; Y is hydrogen or halo; Z is halo, trihalomethyl-or pentahaloethyl; W is nitro, cyano, halo or a radical of the formula: $S(O)_{n'}R$ wherein R is lower alkyl or trihaloalkyl; n' has a value of from 0 to 2; $R^1$ is hydrogen or a substituted or unsubstituted, saturated or unsaturated hydrocarbyl radical; $R^2$ is hydrogen or lower alkyl; n has a value of 0 to 3; $R^3$ is alkoxycarbonyl, alkylcarbonyl, aminocarbonyl, mononuclear aryloxy or carboxy including agronomically acceptable amides, esters or salts thereof or $R^1$ and $R^2$ may be joined together with the nitrogen to which they are attached to form a heterocyclic ring containing one nitrogen atom and from 4 to 8 nuclear carbon atoms.

2. The compound of claim 1 wherein $R^1$ is hydrogen, lower alkyl, lower alkenyl or lower alkynyl; $R^2$ is hydrogen and $R^3$ is lower alkoxycarbonyl or lower alkylcarbonyl an n has a value of 0 to 1.

3. The compound of claim 2 named N-ethoxycarbonylaminooxy-5-(2-chloro-4-trifluoromethylphenoxy)-2-nitrobenzoate.

4. The compound of claim 2 named N-ethoxycarbonyl-N-methylaminooxy-5-(2-chloro-4-trifluromethylphenoxy)-2-nitrobenzoate.

5. A method of controlling weeds which comprises applying to the surface of the growth medium prior to the emergence of the weeds from the growth medium a compound according to claims 1, 2, 3 or 4 in an amount sufficient to control the growth of the weeds.

6. The method of claim 5 wherein the compound is applied at a rate of about 0.1 to about 12 pounds per acre.

7. A method of controlling weeds which comprises applying to weed seedlings a compound according to claims 1, 2, 3 or 4 in an amount sufficient to control the growth of the seedlings.

8. The method of claim 7 wherein the compound is applied at a rate of about 0.1 to about 12 pounds per acre.

9. A herbicidal composition comprising a compound according to claims 1, 2, 3 or 4 and an agronomically acceptable carrier.

10. The composition of claim 9 wherein the carrier is an organic solvent.

11. The composition of claim 9 which also comprises a surfactant.

* * * * *